US008084606B2

(12) United States Patent
Mohan Rao et al.

(10) Patent No.: US 8,084,606 B2
(45) Date of Patent: Dec. 27, 2011

(54) PROCESS FOR PREPARATION OF SUBSTANTIALLY OPTICALLY PURE LEVOROTATORY AND DEXTROROTATORY ENANTIOMERS OF CETIRIZINE USING NOVEL INTERMEDIATES

(75) Inventors: Dodda Mohan Rao, Hyderabad (IN); Bitra Satyanarayana Rao, Hyderabad (IN)

(73) Assignee: Symed Labs Limited (IN)

( * ) Notice: Subject to any disclaimer, the term of this patent is extended or adjusted under 35 U.S.C. 154(b) by 785 days.

(21) Appl. No.: 11/722,266

(22) PCT Filed: Jun. 15, 2007

(86) PCT No.: PCT/IN2007/000239
§ 371 (c)(1),
(2), (4) Date: Jun. 20, 2007

(87) PCT Pub. No.: WO2008/152650
PCT Pub. Date: Dec. 18, 2008

(65) Prior Publication Data
US 2009/0281318 A1    Nov. 12, 2009

(51) Int. Cl.
*C07D 241/04* (2006.01)
*C07D 295/00* (2006.01)
(52) U.S. Cl. .................................................. 544/383
(58) Field of Classification Search ............. 544/383
See application file for complete search history.

(56) References Cited

U.S. PATENT DOCUMENTS 5,478,941 A * 12/1995 Cossement et al. ........... 544/383
2005/0234046 A1    10/2005 Zhao et al.

FOREIGN PATENT DOCUMENTS

| EP | 0617028 A1 | 9/1994 |
| GB | 2225321 A | 11/1989 |
| IN | 2002MA00629 | * 8/2002 |
| IN | 2002MA00629 | * 3/2005 |
| JP | 02184673 A | 7/1990 |
| WO | 2004092117 A1 | 10/2004 |
| WO | WO 2004092117 | * 10/2004 |
| WO | WO 2005115983 | * 12/2005 |
| WO | 2006094648 A1 | 9/2006 |

OTHER PUBLICATIONS

Wang, et al., Synthesis of (+)-2-[2-[4-[(R)-(4-chlorophenyl)phenylmethyl]-1-piperazinyl]ethoxy]acetic Acid Dihydrochoride (Levocetirizine), Guangxi Daxue Xuebao, Ziran Kexueban, 32(4), 384-386 (2007).*
Notification of Transmittal of the International Search Report and The Written Opinion of the International Searching Authority, or the Declaration.

* cited by examiner

*Primary Examiner* — Noble Jarrell
*Assistant Examiner* — Erich A Leeser
(74) *Attorney, Agent, or Firm* — Caesar, Rivise, Bernstein, Cohen & Pokotilow, Ltd.

(57) ABSTRACT

The present invention relates to a novel and commercially viable process for substantially optically pure levorotatory and dextrorotatory enantiomers of cetirizine intermediate, 1-[(4-chlorophenyl)phenylmethyl]piperazine, thereby producing substantially optically pure levorotatory and dextrorotatory enantiomers of cetirizine and their pharmaceutical acceptable acid addition salts thereof in high purity and in high yield using novel intermediates.

15 Claims, No Drawings

PROCESS FOR PREPARATION OF SUBSTANTIALLY OPTICALLY PURE LEVOROTATORY AND DEXTROROTATORY ENANTIOMERS OF CETIRIZINE USING NOVEL INTERMEDIATES

FIELD OF THE INVENTION

The present invention provides a novel and commercially viable process for substantially optically pure levorotatory and dextrorotatory enantiomers of cetirizine intermediate, 1-[(4-chlorophenyl)phenylmethyl]piperazine, thereby producing substantially optically pure levorotatory and dextrorotatory enantiomers of cetirizine and their pharmaceutical acceptable acid addition salts thereof in high purity and in high yield using novel intermediates.

BACKGROUND OF THE INVENTION

UK patent No. GB 2,225,321 discloses enantiomers of 2-[2-[4-[(4-chlorophenyl)phenylmethyl]-1-piperazinyl]ethoxy]acetic acid dihydrochloride, known as a non-sedative antihistamine drug under the generic name of cetirizine. Cetirizine is represented by the following structure:

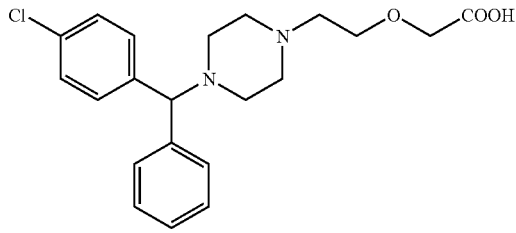

Processes for the preparation of cetirizine and related compounds were disclosed in the UK patent No. GB 2,225,321, U.S. Pat. No. 5,478,941 and PCT patent publication No. WO 2006/094648 A1.

In the preparation of substantially optically pure levorotatory and dextrorotatory enantiomers of cetirizine, substantially optically pure levorotatory and dextrorotatory enantiomers of 1-[(4-chlorophenyl)phenylmethyl]piperazine of formula I:

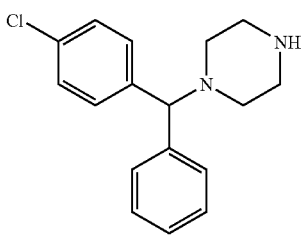

is a key intermediate. According to the UK patent No. GB 2,225,321, the enantiomers of 1-[(4-chlorophenyl)phenylmethyl)piperazine are obtained by chemical resolution of the racemic form, using conventional methods, in particular, by salt formation with a suitable selected optical isomer of tartaric acid.

The major disadvantages of the process are on one hand, that the yield of the resolution step of the racemic 1-[(4-chlorophenyl)phenylmethyl]piperazine is extremely low and, on the other hand, that the optical purity of the dextrorotatory and levorotatory enantiomers so obtained is insufficient and does not allow the final product to be prepared with an optical purity greater than 95%.

The U.S. Pat. No. 5,478,941 disclosed process for preparing levorotatory and dextrorotatory enantiomers of 1-[(4-chlorophenyl)phenyl methyl]-4-[(4-methylphenyl)sulfonyl]piperazine and also preparation of the substantially optically pure enantiomers of 1-[(4-chlorophenyl)phenylmethyl]piperazine using enantiomers of 1-[(4-chlorophenyl)phenylmethyl]-4-[(4-methyl phenyl)sulfonyl]piperazine.

The PCT patent publication No. WO 2006/094648 A1 disclosed the preparation of levocetirizine using the resolution of racemic 2-[4-[4-chlorobenzhydryl]piperazin-1-yl] ethoxyacetamide with (S)-pyrrolidine-5-carboxylic acid and followed by hydrolysis.

Since resolution is performed at an advanced intermediate, there in a loss of costly intermediates and so, the process is commercially not viable.

However, a need still remains for an improved and commercially viable process of preparing substantially optically pure levorotatory and dextrorotatory enantiomers of cetirizine, and their pharmaceutical acceptable acid addition salts thereof, that will solve the aforesaid problems associated with processes described in the prior art and will be suitable for large scale preparation, in terms of simplicity, purity and yield of the product.

One object of the present invention is to provide a novel process for preparation of substantially optically pure levorotatory and dextrorotatory enantiomers of cetirizine intermediate, 1-[(4-chlorophenyl)phenylmethyl]piperazine.

Another object of the present invention is to provide a process for preparing substantially optically pure levorotatory and dextrorotatory enantiomers of cetirizine and their pharmaceutical acceptable acid addition salts thereof in high purity and in high yield using novel intermediates.

Another object of the present invention is to provide a novel intermediates for the preparation of substantially optically pure levorotatory and dextrorotatory enantiomers of 1-[(4-chlorophenyl)phenylmethyl]piperazine.

DETAILED DESCRIPTION OF THE INVENTION

In accordance with the present invention, there is provided a novel process for preparing substantially optically pure levorotatory and dextrorotatory enantiomers of 1-[(4-chlorophenyl)phenylmethyl]piperazine of formula I:

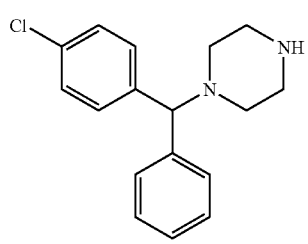

which comprises:

a) reacting substantially optically pure levorotatory and dextrorotatory enantiomers of (4-chlorophenyl)phenylmethylamine of formula II:

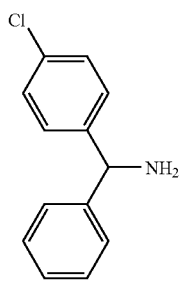

with sulfonamide compound of formula III:

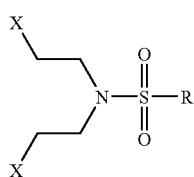

wherein X is a leaving group such as halogen or (4-methylphenyl)sulfonyloxy or methylsulfonyloxy group; and R is alkyl, cycloalkyl, unsubstituted or substituted phenyl provided R is not p-tolyl;
in presence of a base to give substantially optically pure levorotatory and dextrorotatory enantiomers of piperazine sulfonamide compound of formula IV:

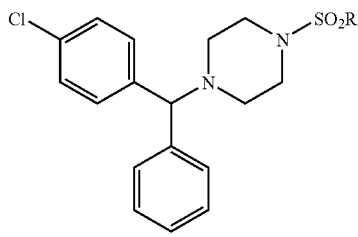

wherein R is as defined above; and
b) deprotecting the piperazine sulfonamide compound of formula IV to give substantially optically pure levorotatory and dextrorotatory enantiomers of 1-[(4-chlorophenyl)phenylmethyl]piperazine of formula I.

Preferably R is phenyl, alkoxy substituted phenyl, halo substituted phenyl, nitro substituted phenyl, amino substituted phenyl or acetyl amino substituted phenyl, and more preferably R is phenyl, methoxy substituted phenyl, chloro substituted phenyl or nitro substituted phenyl.

Except otherwise stated the term alkyl refers to $C_1$ to $C_{10}$ straight or branched alkyl group, the term cycloalkyl refers to $C_3$-$C_6$-cycloalkyl, and the term alkoxy refers to $C_1$-$C_5$-alkoxy.

Halogen represents fluorine, chlorine, bromine or iodine. Preferably X is halogen, more preferably chlorine or bromine, and still more preferably chlorine.

Substantially optically pure levorotatory and dextrorotatory enantiomers of cetirizine and their pharmaceutically acceptable acid addition salts can be prepared by using the compounds of formula I by known methods for example as described in the UK patent No. GB 2,225,321.

Piperazine sulfonamide compound of formula IV are novel and forms part of the invention.

The base used in step (a) is an organic base or an inorganic base. Preferable organic base is tributylamine, N,N-dimethylaniline, 4-dimethylaminopyridine, ethyldiisopropylamine, N-ethylmorpholine, 2,4,6-trimethylpyridine or triethylamine, and more preferable organic base is N,N-dimethylaniline or tributylamine. Preferably, the inorganic base is an acid scavenger such as sodium carbonate. The reaction may be carried out in the presence of a solvent or the base used as acid scavenger may also be used as solvent.

The piperazine sulfonamide compound of formula IV obtained above may be isolated as a solid before proceeding to the next step or the reaction mass containing piperazine sulfonamide can be used directly in the next step without isolation.

The isolation of piperazine sulfonamide compound of formula IV can be carried out by the method known in the art such as cooling, by using an anti solvent, partial evaporation etc.

The deprotection reaction of the enantiomerically pure piperazine sulfonamide compound of formula IV is carried out by methods known for the deprotection of an amine group of the sulfonamides. Preferably, enantiomerically pure piperazine sulfonamide compound of formula IV is hydrolyzed with hydrobromic acid, in acetic acid medium and in the presence or absence of a phenolic compound such as 4-Hydroxy benzoic acid.

In the present specification, by "substantially optically pure", is meant an optical purity greater than 95% and this optical purity corresponds to the percent excess of the optically active isomer present in major amount with respect to the optically active isomer present in minor amount, and determined by high performance liquid phase chromatography (HPLC) on a chiral stationary phase.

Since the deprotection reaction leading to the formation of enantiomers of the compound of formula (I) is non-racemizing, these enantiomers are obtained with an optical purity, which is much greater than 95%, even approaching 100%.

The invention will now be further described by the following examples, which are illustrative rater than limiting.

Reference Example

Preparation of N,N-[bis(chloroethyl)]phenyl sulfonamide

Diethanolamine (0.5 mol) in 2N $Na_2CO_3$ (250 ml) was treated with benzene sulfonyl chloride (0.5 mol) at 65-70° C. The reaction mixture was then heated for 1 hour at 95° C. and cooled. The reaction mixture was poured into ice water and extracted with chloroform. Evaporation of chloroform gave 103 gm of N,N-[bis(hydroxyethyl)]phenyl sulfonamide in 85% yield. The product obtained above was then refluxed with thionylchloride at 110° C. for 1 hour. After cooling, the reaction mass was poured in ice with stirring. The resulting solid was filtered and recrystallised from methanol to give the desired product (84%).

EXAMPLES

Example-1

Preparation of Levocetirizine Dihydrochloride

Step-I: Levorotatory (−)-1-[(4-Chlorophenyl)phenylmethyl]-4-[(phenyl)sulfonyl]piperazine Levorotatory (−)-(4-chlorophenyl)phenylmethylamine (45 gm), N,N-[bis(2-chloroethyl)]phenyl sulfonamide (67.5 gm) and tributyl amine (80 ml) are taken in a 500 ml round-bottomed flask. The mixture is heated to reflux and refluxed for 4 hours. The reaction mixture is cooled to 80° C. and methanol (185 ml) is added. The reaction mixture is refluxed for 30 minutes and cooled to 0-5° C., stirred for 1 hour and the precipitate formed is filtered and washed with methanol (100 ml) and dried to obtain 74 gm of levorotatory (−)-1-[(4-chlorophenyl)phenylmethyl]-4-[(phenyl)sulfonyl]piperazine [Melting Range: 116-118° C.; $[\alpha]_D^{25}$=−36.5 (c=1, toluene); Chiral Purity by HPLC: 99.8%].

Step-II: Levorotatory (−)-1-[(4-Chloro phenyl)phenylmethyl]piperazine

Levorotatory (−)-1-[(4-chlorophenyl)phenylmethyl]-4-[(phenyl)sulfonyl]piperazine (100 gm) is added to 30% hydrobromic acid in acetic acid (271 ml). The suspension is stirred at 25-30° C. for 1 hour, heated to 60° C. and maintained for 4 hours. Water (1000 ml) is added to reaction mass and cooled to 25-30° C. The precipitate formed is filtered off and washed with water (250 ml). Toluene (500 ml) is added to the aqueous layer and basified with 50% aqueous solution of sodium hydroxide. Toluene layer is separated, distilled under reduced pressure and the residue left is recrystallised from boiling hexane (160 ml). The solution is filtered and allowed to recrystallise first at ambient temperature, and then in an ice bath. The product is filtered off, washed with hexane and dried to obtain 55 gm of levorotatory (−)-1-[(4-chloro phenyl)phenylmethyl]piperazine [M.R: 89-93° C.; $[\alpha]_D^{25}$=−15.6 (c=1, methanol); Chiral Purity by HPLC: 99.7%].

Step-III: Levorotatory (−)-[2-[4-[(4-Chlorophenyl)-phenylmethyl]-1-piperazinyl]ethanol Levorotatory (−)-1-[(4-chlorophenyl)phenylmethyl]piperazine (50 gm), 2-chloroethanol (31.4 gm), potassium iodide (1.3 gm) and sodium carbonate (40.8 gm) are taken in toluene (446 ml) and refluxed for 24 hours. The reaction mixture is cooled to 25-35° C., washed with water (285 ml) followed by two times with water (each time 185 ml). The layers are separated. Toluene is evaporated from organic layer under reduced pressure to yield 58 gm of levorotatory (−)-[2-[4-[(4-Chlorophenyl)-phenylmethyl]-1-piperazinyl]ethanol.

Step-IV: Preparation of Levocetirizine dihydrochloride

Levorotatory (−)-[2-[4-[(4-chlorophenyl)-phenylmethyl]-1-piperazinyl]ethanol (100 gm) is dissolved in dimethylformamide (200 ml) and cooled to 10-15° C. Potassium hydroxide (44 gm) is added to the reaction mixture and maintained for 30 minutes. Sodium monochloroacetate (85 gm) is added to the reaction mixture and further maintained for 1 hour at 10-15° C. The temperature of the reaction mixture is then raised to 25° C. and maintained for 1 hour. The temperature of the reaction mixture is further raised to 35-38° C. and maintained for 3 hours. Water (1800 ml) is added to the reaction mixture and the $p^H$ of the reaction mixture is adjusted to 9.6-9.8 with hydrochloric acid. The reaction mixture is then washed five times with ethyl acetate (each time 400 ml) and the layers are separated. The $p^H$ of the aqueous layer is adjusted to 5-5.5 with hydrochloric acid and extracted with dichloromethane (400 ml) followed by two times with dichloromethane (each time 100 ml). The extracted dichloromethane layer is washed with water and solvent distilled off to afford 100 gm of levocetirizine as a residue, which is dissolved in acetone (1000 ml). Activated carbon (10 gm) is added, stirred and filtered. To the filtrate hydrochloric acid gas is passed till the $p^H$ of the reaction mass is 2. The reaction mass is refluxed for 30 minutes, cooled to 25-35° C. and filtered. The product is washed with acetone (100 ml) and dried to constant weight to obtain 105 gm of Levocetirizine dihydrochloride [M.R: 215-220° C.; $[\alpha]_{365}^{25}$: +12.8 (c=1, water); Chiral Purity by HPLC: 99.8%].

Example 2

Preparation of Dextrocetirizine Dihydrochloride

Dextrocetirizine dihydrochloride (Chiral Purity by HPLC: 99.7%) is prepared by using the method described in the above example 1, but replacing levorotatory (−)-(4-chlorophenyl)phenylmethylamine with dextrorotatory enantiomer.

Example 3

Preparation of Levorotatory (−)-1-[(4-chlorophenyl) phenylmethyl]-4-[(4-methoxy phenyl)sulfonyl]piperazine Levorotatory (−)-(4-Chlorophenyl)phenylmethyl amine (26 gm), N,N-bis(2-Chloroethyl)-4-methoxybenzene sulfonamide (41 gm) and tributylamine (46 ml) are taken in a round bottomed flask and refluxed for 4 hours. The reaction mixture is cooled to 80° C. and methanol (105 ml) is added. The reaction mixture is refluxed for 30 minutes, cooled to 0-5° C., stirred for 1 hour, the precipitate formed is filtered and washed with methanol (50 ml) and then dried to obtain 47.2 gm of levorotatory (−)-1-[(4-chlorophenyl)phenylmethyl]-4-[(4-methoxy phenyl)sulfonyl]piperazine [M.R: 157-159° C., $[\alpha]_D^{25}$: −39.7].

Example 4

Preparation of Levorotatory (−)-1-[(4-chlorophenyl) phenylmethyl]-4-[(4-chloro phenyl)sulfonyl]piperazine Levorotatory(−)-(4-chlorophenyl)phenylmethylamine (40 gm), N,N-bis(2-chloroethyl)-4-chlorobenzenesulfonamide (64 gm) and tributyl amine (71 ml) are refluxed for 4 hours. The reaction mixture is cooled to 80° C. and then methanol (165 ml) is added. The reaction mixture is refluxed for 30 minutes, cooled to 0-5° C., filtered, washed with methanol (100 ml) and then dried to obtain 72.7 gm of (−)-1-[(4-chlorophenyl)phenylmethyl]-4-[(4-chlorophenyl)sulfonyl]piperazine [M.R: 155-157° C., $[\alpha]_D^{25}$: −41.7].

We claim:

1. A process for the preparation of substantially optically pure levorotatory and dextrorotatory enantiomers of 1-[(4-chlorophenyl)phenylmethyl]piperazine of formula I:

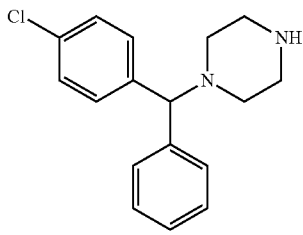

I which comprises:
a) reacting substantially optically pure levorotatory and dextrorotatory enantiomers of (4-chlorophenyl)phenyl-methylamine of formula II:

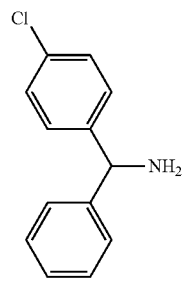

II with sulfonamide compound of formula III:

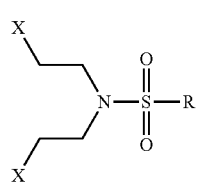

III wherein X is a leaving group selected from the group consisting of halogen, (4-methylphenyl)sulfonyloxy, and methylsulfonyloxy group; and R is alkyl, cycloalkyl, phenyl, halo-substituted phenyl, nitro-substituted phenyl, amino-substituted phenyl, or acetyl amino-substituted phenyl;
in the presence of a base to give substantially optically pure levorotatory and dextrorotatory enantiomers of piperazine sulfonamide compound of formula IV:

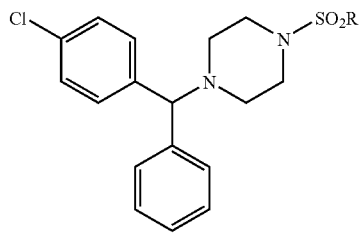

IV wherein R is as defined above; and
b) deprotecting the piperazine sulfonamide compound of formula IV to give substantially optically pure levorotatory and dextrorotatory enantiomers of 1-[(4-chlorophenyl)phenylmethyl]piperazine of formula I.

2. The process as claimed in claim 1, wherein the leaving group X is a halogen.

3. The process as claimed in claim 2, wherein the halogen is fluorine, chlorine, bromine or iodine.

4. The process as claimed in claim 3, wherein the halogen is chlorine or bromine.

5. The process as claimed in claim 4, wherein the halogen is chlorine.

6. The process as claimed in claim 1, wherein the R is phenyl, halo substituted phenyl, nitro substituted phenyl, amino substituted phenyl or acetyl amino substituted phenyl.

7. The process as claimed in claim 6, wherein the R is phenyl, chloro substituted phenyl or nitro substituted phenyl.

8. The process as claimed in claim 1, wherein the base used in step (a) is an organic base or an inorganic base.

9. The process as claimed in claim 8, wherein the organic base is tributylamine, N,N-dimethylaniline, 4-dimethylaminopyridine, ethyldiisopropylamine, N-ethylmorpholine, 2,4,6-trimethylpyridine or triethylamine.

10. The process as claimed in claim 9, wherein the organic base is tributylamine or N,N-dimethylaniline.

11. The process as claimed in claim 8, wherein the inorganic base is an acid scavenger such as sodium carbonate.

12. Substantially optically pure levorotatory and dextrorotatory enantiomers of piperazine sulfonamide compound of formula IV:

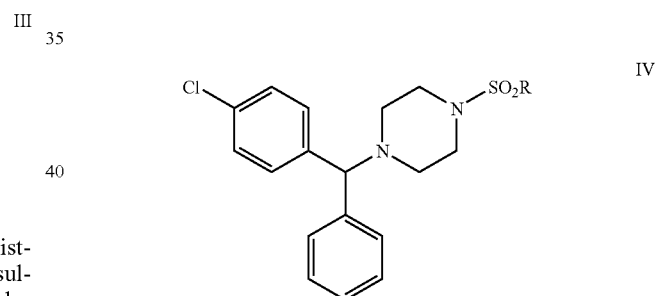

IV wherein R is alkyl, cycloalkyl, phenyl, halo-substituted phenyl, nitro-substituted phenyl, amino-substituted phenyl, or acetyl amino-substituted phenyl.

13. The compound as claimed in claim 12, wherein the R is phenyl, halo substituted phenyl, nitro substituted phenyl, amino substituted phenyl or acetyl amino substituted phenyl.

14. The compound as claimed in claim 13, wherein the R is phenyl, chloro substituted phenyl, nitro substituted phenyl, amino substituted phenyl or acetyl amino substituted phenyl.

15. The compound as claimed in claim 12, wherein the levorotatory and dextrorotatory enantiomers of piperazine sulfonamide compound of formula IV having chiral purity of above 99%.

* * * * *